(12) United States Patent
Gertz et al.

(10) Patent No.: US 9,999,731 B2
(45) Date of Patent: Jun. 19, 2018

(54) SELF-LUBRICATING MEDICAL SYRINGES

(71) Applicant: ZebraSci, Inc, Temecula, CA (US)

(72) Inventors: Frederick Talley Gertz, Riverside, CA (US); Jaan Noolandi, La Jolla, CA (US); Robert James Schultheis, Temecula, CA (US); Daniel Alden Wilcox, Escondido, CA (US)

(73) Assignee: ZebraSci, Inc, Temecula, CA (US)

( * ) Notice: Subject to any disclaimer, the term of this patent is extended or adjusted under 35 U.S.C. 154(b) by 198 days.

(21) Appl. No.: 15/182,889

(22) Filed: Jun. 15, 2016

(65) Prior Publication Data

US 2016/0367758 A1  Dec. 22, 2016

Related U.S. Application Data

(60) Provisional application No. 62/180,196, filed on Jun. 16, 2015.

(51) Int. Cl.
*A61M 5/315* (2006.01)

(52) U.S. Cl.
CPC .............................. *A61M 5/31513* (2013.01)

(58) Field of Classification Search
CPC ............ A61M 5/31513; A61M 5/1452; A61M 5/14526; A61M 5/2422; A61M 5/2425; A61M 5/2429; A61M 5/281; A61M 5/282; A61M 5/283; A61M 5/284; A61M 5/285; A61M 5/315; A61M 5/31511; A61M 5/31515; A61M 2205/073
See application file for complete search history.

(56) References Cited

U.S. PATENT DOCUMENTS

| 2,419,401 A | 4/1947 | Hinds |
| 2,950,717 A * | 8/1960 | Bouet ...................... A61J 1/062 604/214 |
| 3,517,816 A * | 6/1970 | Hoppen .............. A47L 15/4229 210/266 |
| 3,656,480 A | 4/1972 | Rubricius |
| 4,266,557 A | 5/1981 | Merry |
| 4,613,326 A | 9/1986 | Szwarc |
| 4,792,329 A * | 12/1988 | Schreuder ............. A61M 5/284 604/191 |
| 4,986,820 A | 1/1991 | Fischer |
| 5,531,683 A * | 7/1996 | Kriesel ............... A61M 5/2429 604/416 |
| 5,569,191 A * | 10/1996 | Meyer ................... A61F 9/0008 604/201 |
| 5,685,846 A * | 11/1997 | Michaels, Jr. .... A61M 5/31596 604/181 |

(Continued)

FOREIGN PATENT DOCUMENTS

| CN | 204840528 | 12/2015 |
| WO | WO2015141462 | 9/2015 |

*Primary Examiner* — Quynh-Nhu H Vu
(74) *Attorney, Agent, or Firm* — Lumen Patent Firm

(57) ABSTRACT

A self-lubricating medical syringe is provided for self-lubricating the inner surface of a prefilled syringe barrel. The syringe has a plunger distinguishing a compressible porous cylinder, which can be infused with a lubricant and is sandwiched in between a proximal and distal rubber tip. The self-lubricating medical syringe will be able to compensate for any missing lubricant along the inner surface of the syringe barrel and will also be able to provide for a uniform motion of the plunger.

4 Claims, 2 Drawing Sheets

(56) References Cited

U.S. PATENT DOCUMENTS

| | | | |
|---|---|---|---|
| 5,807,323 A * | 9/1998 | Kriesel | A61M 5/14526 604/232 |
| 6,171,286 B1 | 1/2001 | Gross | |
| 6,485,471 B1 * | 11/2002 | Zivitz | A61M 5/1452 604/181 |
| 7,011,650 B2 * | 3/2006 | Rosoff | A61M 5/282 604/191 |
| 7,077,826 B1 | 7/2006 | Gray | |
| 7,988,676 B1 | 8/2011 | Gray | |
| 8,814,823 B2 * | 8/2014 | Pickhard | A61M 5/284 604/82 |
| 2007/0060870 A1 * | 3/2007 | Tolle | A61M 5/14244 604/65 |
| 2007/0167908 A1 * | 7/2007 | Kirchhofer | A61M 5/2448 604/82 |
| 2009/0171285 A1 | 7/2009 | Wang | |
| 2010/0030159 A1 | 2/2010 | Li | |
| 2011/0082430 A1 | 4/2011 | Conzone | |
| 2012/0101453 A1 | 4/2012 | Boettger | |
| 2014/0276039 A1 * | 9/2014 | Cowan | A61M 5/31513 600/432 |
| 2016/0008534 A1 * | 1/2016 | Cowan | A61M 5/1782 600/432 |
| 2016/0038684 A1 * | 2/2016 | Lum | A61M 5/38 141/2 |
| 2016/0317738 A1 * | 11/2016 | Cross | A61M 5/1454 |

\* cited by examiner

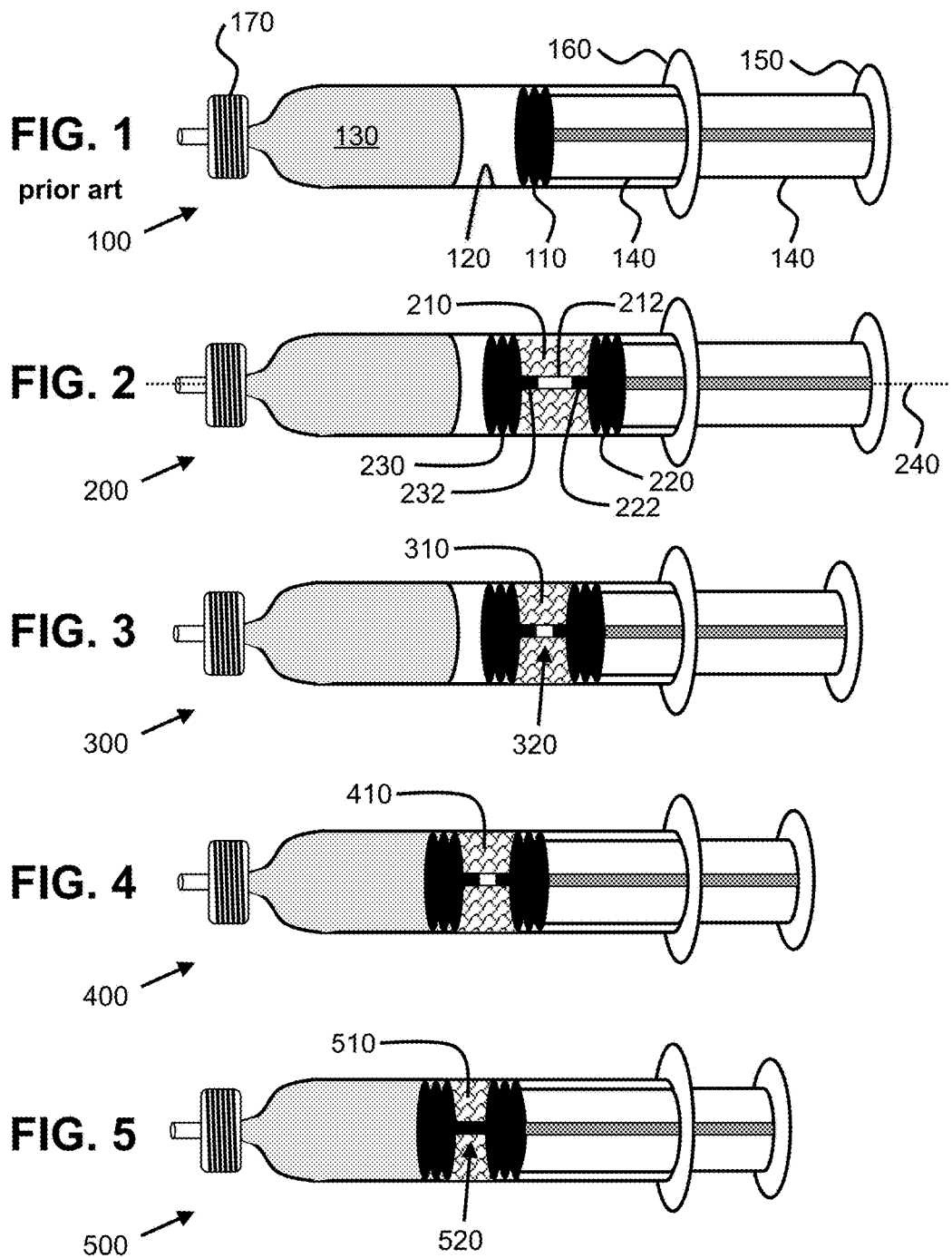

SELF-LUBRICATING MEDICAL SYRINGES

CROSS-REFERENCE TO RELATED APPLICATIONS

This application claims priority from U.S. Provisional Patent Application 62/180,196 filed Jun. 16, 2015, which is incorporated herein by reference.

FIELD OF THE INVENTION

This invention relates to lubrication of medical syringes or self-lubricating syringes.

BACKGROUND OF THE INVENTION

Medical syringes are used to inject a fluid or medication inside a body. A plunger is pushed along the inside of the syringe barrel, which then moves the fluid through a needle inside the body. FIG. 1 shows a typical medical syringe barrel 100 with plunger 110. Plunger 110 is typically a rubber tip with for example three ribs.

Lubrication of the inside surface 120 of the syringe barrel 100 is crucial to reduce the friction between the plunger 110 and the inner surface of the syringe barrel and ensure effective injection of fluid 130.

Syringe barrels are normally lubricated by spraying the inside of the syringe barrel using a spraying nozzle, which is fixed in space in the middle of the cylindrical barrel, and which in turn is moved up and down past the sprayer while it is active.

This method of lubrication generally works well, but is subject to irregularities, which can arise when the sprayer does not spray uniformly in all directions or may not be centered in the middle of the syringe barrel. The present invention advances the technology of syringe barrels by addressing at least some of the current problems with lubrication of these syringe barrels.

SUMMARY OF THE INVENTION

A self-lubricating medical syringe is provided for self-lubricating the inner surface of a prefilled syringe barrel. A cylindrical barrel distinguishes a plunger that fits in the cylindrical barrel and can be moved along the cylindrical barrel. The plunger further distinguishes a compressible porous cylinder (e.g. made out of foam or rubber) sandwiched in between a proximal rubber tip at its proximal end and a distal rubber tip at its distal end. The rubber tips could have one or more ribs. The compressible porous cylinder has a hole in axial direction of the cylindrical barrel. The compressible porous cylinder can be infused with a lubricant.

The proximal rubber tip has a proximal protuberance at the side facing the compressible porous cylinder, which fits within the hole of the compressible porous cylinder. The distal rubber tip has a distal protuberance at the side facing the compressible porous cylinder, which fits within the hole of the compressible porous cylinder. The proximal protuberance and distal protuberance are aligned in the axial direction and are at a distance from each other within the hole of the compressible porous cylinder when the compressible porous cylinder is in a non-compressed state. The distance between the proximal protuberance and distal protuberance gets smaller when the compressible porous cylinder is in being compressed when the plunger is being pushed along the cylindrical barrel.

The compressible porous cylinder, when being compressed, forces out the lubricant onto the inner surface of the cylindrical barrel and thereby self-lubricates the inner surface of the cylindrical barrel.

The advantage of the self-lubricating medical syringe compared to traditional syringes is that it will be able to compensate for any missing lubricant along the inner surface of the syringe barrel and will also be able to provide for a uniform motion of the plunger.

BRIEF DESCRIPTION OF THE DRAWINGS

FIG. 1 shows a syringe barrel 100 according to the prior art. Syringe barrel 100 has a plunger 110, which typically is a rubber tip with for example three ribs. Plunger 110 can be pushed by end-piece 150 via rod 140. Using end-piece 150 and barrel holder lip 160, plunger 110 can be pushed along the inner surface 120 of syringe barrel 110 therewith moving fluid 130 through a needle (not shown). A needle protector 170 is shown to protect the needle.

FIGS. 2-5 show a syringe barrel according to an exemplary embodiment of the invention where the plunger is defined as a compressible cylindrical foam 210 sandwiched between a proximal rubber tip 220 and a distal rubber tip 230. FIG. 2 shows syringe barrel 200 with compressible cylindrical foam 210 in an uncompressed state. FIG. 3 shows syringe barrel 300 with compressible cylindrical foam 310 in a compressed state. FIG. 4 shows syringe barrel 400 with compressible cylindrical foam 410 in a compressed state, but further along the barrel than compressible cylindrical foam 310 shown in FIG. 3. FIG. 5 shows syringe barrel 500 with compressible cylindrical foam 510 in a maximum compressed state as proximal rubber tip 220 and a distal rubber tip 230 are preventing further compression since they are contacting each other as indicated by 520.

DETAILED DESCRIPTION

Figure 6:
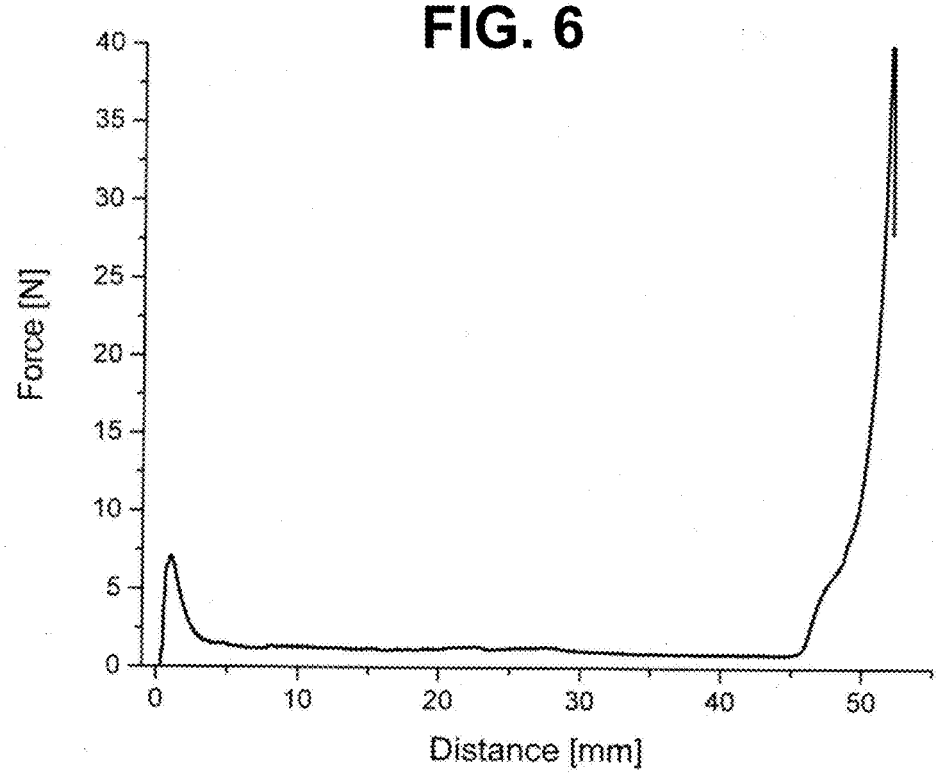
FIG. 6 shows according to an exemplary embodiment of the invention measured glide force when a foam (rubber) cylinder infused with oil is pushed down the syringe barrel.

FIG. 2 shows a self-lubricating medical syringe 200 with a cylindrical barrel and a plunger that fits in the cylindrical barrel. The plunger distinguishes a proximal end and a distal end. The plunger is defined by a compressible porous cylindrical foam or rubber 210 sandwiched in between a proximal rubber tip 220 at the proximal end and a distal rubber tip 230 at the distal end. In this example, the rubber tips each have three ribs, however any type of plunger tip could be used. Like in FIG. 1, the plunger can be pushed into the cylindrical barrel.

The compressible foam 210 has a hole 212 in axial direction 240 of the cylindrical barrel or medical syringe. Hole 212 is through the entire compressible foam 210.

The proximal rubber tip 220 has a proximal protuberance 222 at the side facing the compressible foam 210. The proximal protuberance 222 fits within hole 212 of the compressible foam 210. The distal rubber tip 230 has a distal protuberance 232 at the side facing the compressible foam 210. The distal protuberance 232 also fits within hole 212 of the compressible foam 210. The proximal protuberance 222, distal protuberance 232 and hole 212 are aligned in the axial direction. The proximal and distal rubber tips are not connected to each other to enable that the compressible foam can be compressed/squeezed. The proximal and distal rubber tips 232, 222 are able to move with respect to each other within hole 212 depending on the relative movements of proximal rubber tip 220 and distal rubber tip 230.

When the compressible cylindrical foam 210 is in an uncompressed state like shown in FIG. 2, the proximal protuberance 222 and distal protuberance 232 are at a distance from each other within hole 212 of the compressible cylindrical foam 210, which is illustrated by the white area in hole 212 in between the two protuberances, 222, 232.

The selection of the compressible porous foam or rubber varies on the modulus of the compressible foam/rubber soaked with the lubricant. The separation of the proximal and distal protuberances in uncompressed state of the compressible foam depends on the compressibility of the foam or rubber. In one example, the initial separation between the proximal and distal protuberances is about 40% of the length of the uncompressed foam or rubber (e.g. initial gap is 4 mm when length of foam or rubber is 10 mm).

As shown in FIGS. 3-4, when the compressible cylindrical foam 210 is compressed resulting from the proximal rubber tip 220 being pushed along the cylindrical barrel, the distance between the proximal protuberance 222 and distal protuberance 232 gets smaller, which is illustrated by the relatively smaller white area in hole 212 in between the two protuberances, 222, 232 when FIGS. 3-4 are compared to FIG. 2. FIG. 5 shows an example where the compressible cylindrical foam 210 is maximally compressed due to the fact that the proximal protuberance 222 touches the distal protuberance 232.

The compressible foam 210 is porous and can be infused with a lubricant (e.g. oil or an oil/water emulsion). When the compressible cylindrical foam 210 is being compressed the lubricant is forced out from the compressible cylindrical foam 210 onto the inner surface of the cylindrical barrel and thereby self-lubricating the inner surface of the cylindrical barrel.

The compressible foam 210 is selected and designed so that when compressed a desired amount of lubricant is squeezed onto the interface between the compressible foam 210 and the inner surface of the syringe barrel to provide as much lubrication as possible. In another embodiment, the compressible foam cylinder has striations at an angle on the surface of the compressible foam cylinder, causing the plunger to rotate during its motion, thereby further enhancing the lubrication process.

In one example, the initial uncompressed diameter of the compressible foam may be slightly smaller (e.g. by a fraction of a millimeter) than the inner diameter of the syringe barrel yet when compressed lubricant is forced to the inner surface when it is initially inserted into the barrel of the syringe.

In another example, the initial uncompressed diameter of the compressible foam may be slightly larger (e.g. by a fraction of a millimeter) than the inner diameter of the syringe barrel so that lubricant is forced to the inner surface when it is initially inserted into the barrel of the syringe.

The plunger as shown for example shown in FIG. 2 and when infused with a lubricant can be used to lubricate the inner surface of a syringe barrel instead of using a spraying nozzle. The advantage of this method is that some lubricating materials may be difficult to spray, whereas the compressible foam can be incubated in the lubrication material ahead of time, and a simple down motion of this lubricating device inside the barrel can achieve the desired lubrication purpose.

In yet another embodiment of this invention a relatively more flexible rubber tip can be used instead of the distal rubber tip. An advantage of a more flexible rubber tip is that when force is initially applied to the plunger, the plunger tip moves away from the interior wall of the barrel, thereby overcoming or eliminating the brake-loose force which is encountered with a normal rigid rubber tip plunger. When the plunger is first inserted into the filled barrel, a short backward motion of the plunger may be required to make sure that the flexible rubber ribs are in contact with the wall of the barrel. This ensures that there will be no leakage of the medication out of the barrel while the syringe is in storage.

Glide Force Measurement

The determination of the break-loose force and glide force for the syringes was carried out using a Zwick Roell (Kennesaw, Ga.) test device based on standards EN ISO 7886-1, EN ISO11499 and ISO 11040-4. The force applied to a syringe plunger during the injection of a drug formulation via a needle is dissipated in three ways: (a) overcoming the resistance force of the syringe plunger; (b) imparting kinetic energy to the liquid; and (c) forcing the liquid through the needle. In the force versus displacement plots of shown in FIGS. 6-7 three different portions can be identified. The first is related to the force required to displace the plunger, namely the plunger stopper break-loose force (PBF). The maximum value is followed by a plateau (second portion) indicating that the streamline of the formulation through the needle occurs with roughly a constant force. In this portion the average load required 2 N to sustain the movement of the plunger to expel the content of the syringe is called the dynamic glide force (DGF). During the third portion, the force rapidly increases because of the compression of syringe plunger against the end of syringe body.

FIG. 6 shows the measured glide force when a foam rubber cylinder infused with oil is pushed down the syringe barrel using the Zwick Roell instrument. We used an Ompi 1 ml syringe (Newtown, Pa.) and the foam rubber cylinder was infused with Dow Corning oil, with a viscosity of 20 centistokes (cSt). As an example of a porous foam rubber material we used Fents Foam Ear Plugs (Walmart) cut to fit the Ompi 1 ml syringe with a length of 5 mm.

Figure 7:
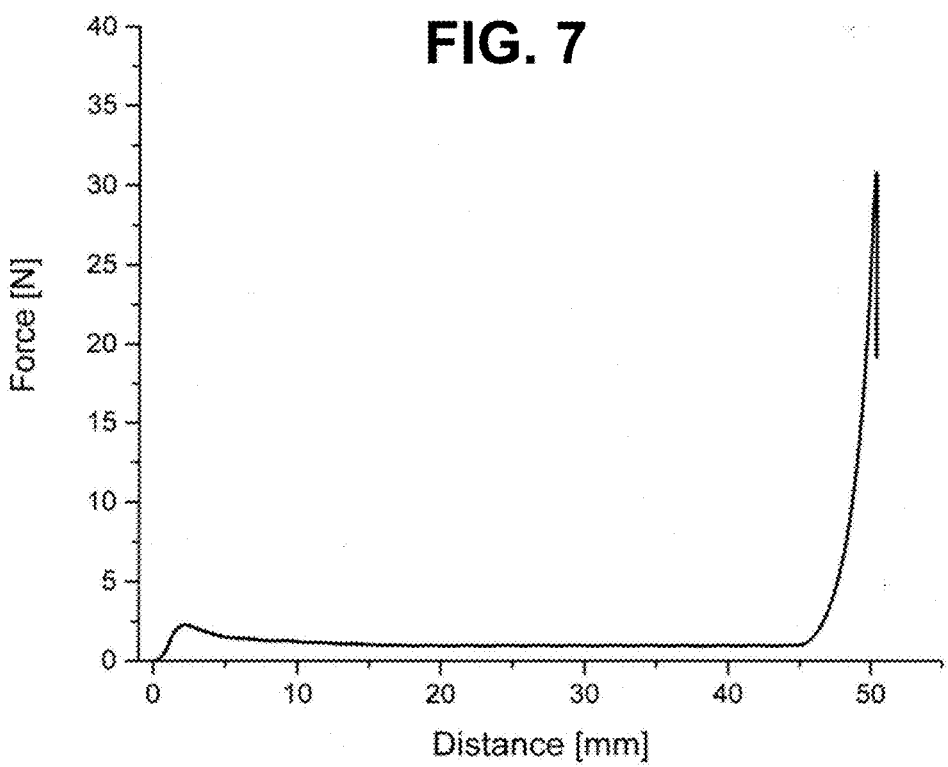
FIG. 7 shows according to an exemplary embodiment of the invention measured glide force when a foam cylinder (sandwiched by two rubber end tips) infused with oil is pushed down the syringe barrel.

FIG. 7 shows the measured glide force when the foam rubber cylinder infused with oil is inserted between two rubber tips or stoppers (West Pharmaceuticals, Scottsdale, Ariz.). As with standard plungers (FIG. 1) the rubber tips or stoppers prevent the drug product from mixing with the lubricant oil.

The measured glide forces in FIGS. 6-7 are virtually identical, showing that the rubber tips or stoppers do not affect the barrel lubrication and is the result of the oil infused foam rubber cylinder moving along the interior surface of the syringe barrel.

What is claimed is:

1. A self-lubricating medical syringe, comprising:
   a cylindrical barrel with a plunger that fits in the cylindrical barrel,
   wherein the plunger has a proximal end and a distal end,
   wherein the plunger can be moved along the cylindrical barrel,
   wherein the plunger distinguishes a compressible porous cylinder sandwiched in between a proximal rubber tip at the proximal end and a distal rubber tip at the distal end,
   wherein the compressible porous cylinder has a hole in axial direction of the cylindrical barrel,
   wherein the compressible porous cylinder can be infused with a lubricant, wherein proximal rubber tip has a proximal protuberance at the side facing the compressible porous cylinder and wherein the proximal protuberance fits within the hole of the compressible porous cylinder, wherein distal rubber tip has a distal protuberance at the side facing the compressible porous cylinder and wherein the distal protuberance fits within the hole of the compressible porous cylinder, wherein the proximal protuberance and distal protuberance are aligned in the axial direction and are at a distance from each other within the hole of the compressible porous cylinder when the compressible porous cylinder is in a non-compressed state, wherein the distance between the proximal protuberance and distal protuberance gets smaller when the compressible porous cylinder is in being compressed when the plunger is being pushed along the cylindrical barrel, and wherein the compressible porous cylinder when being compressed forces out the lubricant onto the inner surface of the cylindrical barrel and therewith self-lubricating the inner surface of the cylindrical barrel.

2. The self-lubricating medical syringe as set forth in claim 1, wherein the compressible porous cylinder is a porous foam or a porous rubber.

3. The self-lubricating medical syringe as set forth in claim 1, wherein the proximal rubber tip has one or more rubber ribs.

4. The self-lubricating medical syringe as set forth in claim 1, wherein the distal rubber tip has one or more rubber ribs.

* * * * *